(12) United States Patent
Nakauchi et al.

(10) Patent No.: US 11,369,580 B2
(45) Date of Patent: Jun. 28, 2022

(54) COMPOSITION FOR TREATING ADULT T CELL LEUKEMIA/LYMPHOMA AND METHOD FOR PRODUCING SAME

(71) Applicant: The University of Tokyo, Bunkyo-ku (JP)

(72) Inventors: Hiromitsu Nakauchi, Tokyo (JP); Tomohiro Ishigaki, Tokyo (JP); Satoshi Yamazaki, Tokyo (JP); Yuki Taya, Tokyo (JP)

(73) Assignee: The University of Tokyo, Bunkyo-ku (JP)

( * ) Notice: Subject to any disclaimer, the term of this patent is extended or adjusted under 35 U.S.C. 154(b) by 273 days.

(21) Appl. No.: 16/323,106

(22) PCT Filed: Aug. 4, 2017

(86) PCT No.: PCT/JP2017/028333
§ 371 (c)(1),
(2) Date: May 13, 2019

(87) PCT Pub. No.: WO2018/025978
PCT Pub. Date: Feb. 8, 2018

(65) Prior Publication Data
US 2019/0269638 A1 Sep. 5, 2019

(30) Foreign Application Priority Data
Aug. 5, 2016 (JP) .............................. JP2016-154646

(51) Int. Cl.
*A61K 31/198* (2006.01)
*A61P 3/02* (2006.01)
*A61P 35/02* (2006.01)

(52) U.S. Cl.
CPC .............. *A61K 31/198* (2013.01); *A61P 3/02* (2018.01); *A61P 35/02* (2018.01)

(58) Field of Classification Search
CPC ........... A61K 31/198; A61P 3/02; A61P 35/02
See application file for complete search history.

(56) References Cited

U.S. PATENT DOCUMENTS

| | | |
|---|---|---|
| 10,383,836 B2 | 8/2019 | Nakauchi et al. |
| 2012/0077748 A1 | 3/2012 | Vidyasagar et al. |
| 2013/0252335 A1 | 9/2013 | Kume et al. |
| 2017/0354626 A1 | 12/2017 | Nakauchi et al. |

FOREIGN PATENT DOCUMENTS

| | | |
|---|---|---|
| JP | 59-53429 A | 3/1984 |
| JP | 62-135420 A | 6/1987 |
| WO | WO 2012/056997 A1 | 5/2012 |
| WO | WO 2016/084850 A1 | 6/2016 |

OTHER PUBLICATIONS

Yoshida et al. (Arg. Biol. Chem. (1969), vol. 33, pp. 43-49 . (Year: 1969).*
International Search Report dated Sep. 12, 2017 in PCT/JP2017/028333 filed Aug. 4, 2017.
Kornberg, A. et al., "Granulocytopenia and Anemia in Rats Fed Diets of Low Casein Content," Science, vol. 103, No. 2682, May 24, 1946, pp. 646-648.
Chin, M. et al., "Nutrition-Immunity Correlation Amino Acid Imbalance and Immunocompetence," Biotherapy, vol. 11, No. 4, Apr. 1997, pp. 518-523, (with unedited computer-generated English translation).
Chin, M. et al., "Establishment of TPN Administration System in Mice and Application to Valine Deficient Amino Acid Imbalance Experiment," The Japanese Journal of Surgical Metabolism and Nutrition, vol. 31, No. 3, Jun. 1997, pp. 147 (with unedited computer-generated English translation).
Nakauchi, Y. et al., "Hematopoietic Stem Cell Transplantation and Clinical Examination," Medical Technology, vol. 40, No. 8, Aug. 2012, pp. 854-859 (with unedited computer-generated English translation).
Okumura, H., "Basic and Current Status of Allogeneic Hematopoietic Stem Cell Transplantation," Medical Journal of Toyama Prefectural Central Hospital, vol. 36, No. 1-2, Mar. 2013, pp. 1-7 (with unedited computer-generated English translation).
Goseki, N. et al., "Treatment of Adenocarcinoma by Combination of Intravenous Nutrition using Special Amino Acid Preparation and Anticancer Drugs (RT-Therapy)," Japanese of Journal of Gastroenterology, vol. 77, No. 1, 1980, pp. 112, (with unedited computer-generated English translation).
Sugiyama, T. et al., "Maintenance of the Hematopoietic Stem Cell Pool by CXCL12-CXCR4 Chemokine Signaling in Bone Marrow Stromal Cell Niches," Immunity, vol. 25, Dec. 2006, pp. 977-988.
Tabbara, I. et al., "Allogeneic Hematopoietic Stem Cell Transplantation," Arch Intern Med, vol. 162, Jul. 22, 2002, pp. 1558-1566.
Yoshida, A. et al., "Pattern of Essential Amino Acid Requirement for Growing Rats Fed on a Low Amino Acid Diet," Agricultural and Biological Chemistry, vol. 33, No. 1 1969, pp. 43-49.
Extended European Search Report dated Mar. 17, 2020, in European Patent Application No. 17837079.7.
Japanese Office Action dated Dec. 3, 2019 in Patent Application No. 2018-531993, 5 pages.
H. Harasawa, et al., "Chemotherapy Targeting Methylthioadenosine Phosphorylase (MTAP) Deficiency in Adult T Cell Leulemia (ATL)" Leukemia, vol. 16, 2002, pp. 1799-1807.
European Office Action dated Apr. 26, 2021 in European Patent Application No. 15864232.2, citing documents AX and AY therein, 4 pages.
Boglarka Gyurkocza, et al., "Conditioning regimens for hematopoietic cell transplantation: one size does not fit all," Blood, vol. 124, No. 3, Jul. 17, 2014, pp. 344-353.
Agnieszka Czechowicz, et al., "Efficient Transplantation via Antibody-based Clearance of Hematopoietic Stem Cell Niches," Science, vol. 318, No. 5854, Nov. 23, 2007, 8 pages.

* cited by examiner

*Primary Examiner* — Sahar Javanmard
(74) *Attorney, Agent, or Firm* — Oblon, McClelland, Maier & Neustadt, L.L.P.

(57) ABSTRACT

A nutrition formulation, which is substantially free of at least one of valine and methionine and which is capable of parenteral or enteral administration. The nutrition formulation supplies sufficient nutrients to sustain life for at least three weeks by successive administration. A composition containing the nutrition formulation can be used for treating adult cell leukemia/lymphoma.

8 Claims, 14 Drawing Sheets

FIG. 1

| Amino acid content (mg/L) | Conventional (Complete) | Valine deficient (-Val) | Methionine deficient (-Met) |
|---|---|---|---|
| Alanine | 2.225 | 2.225 | 2.225 |
| Arginine HCl | 73.75 | 73.75 | 73.75 |
| Arginine | 100 | 100 | 100 |
| Anhydrous asparagine | 25 | 25 | 25 |
| Asparagine $H_2O$ | 3.75 | 3.75 | 3.75 |
| Aspartic acid | 13.325 | 13.325 | 13.325 |
| Cysteine 2HCl | 48.245 | 48.245 | 48.245 |
| Cysteine HCl · $H_2O$ | 8.78 | 8.78 | 8.78 |
| Glutamic acid | 13.675 | 13.675 | 13.675 |
| Glutamine | 332.5 | 332.5 | 332.5 |
| Glycine | 14.375 | 14.375 | 14.375 |
| Histidine HCl · $H_2O$ | 15.74 | 15.74 | 15.74 |
| Histidine | 7.5 | 7.5 | 7.5 |
| Hydroxyproline | 10 | 10 | 10 |
| Isoleucine | 297.35 | 297.35 | 297.35 |
| Leucine | 54.525 | 54.525 | 54.525 |
| Lysine HCl | 65.625 | 65.625 | 65.625 |
| Methionine | 16.12 | 16.12 | 0 |
| Phenylalanine | 25.24 | 25.24 | 25.24 |
| Proline | 18.625 | 18.625 | 18.625 |
| Serine | 28.125 | 28.125 | 28.125 |
| Threonine | 36.725 | 36.725 | 36.725 |
| Tryptophan | 7.01 | 7.01 | 7.01 |
| Tyrosine 2Na · $H_2O$ | 42.31 | 42.31 | 42.31 |
| Valine | 36.425 | 0 | 36.425 |

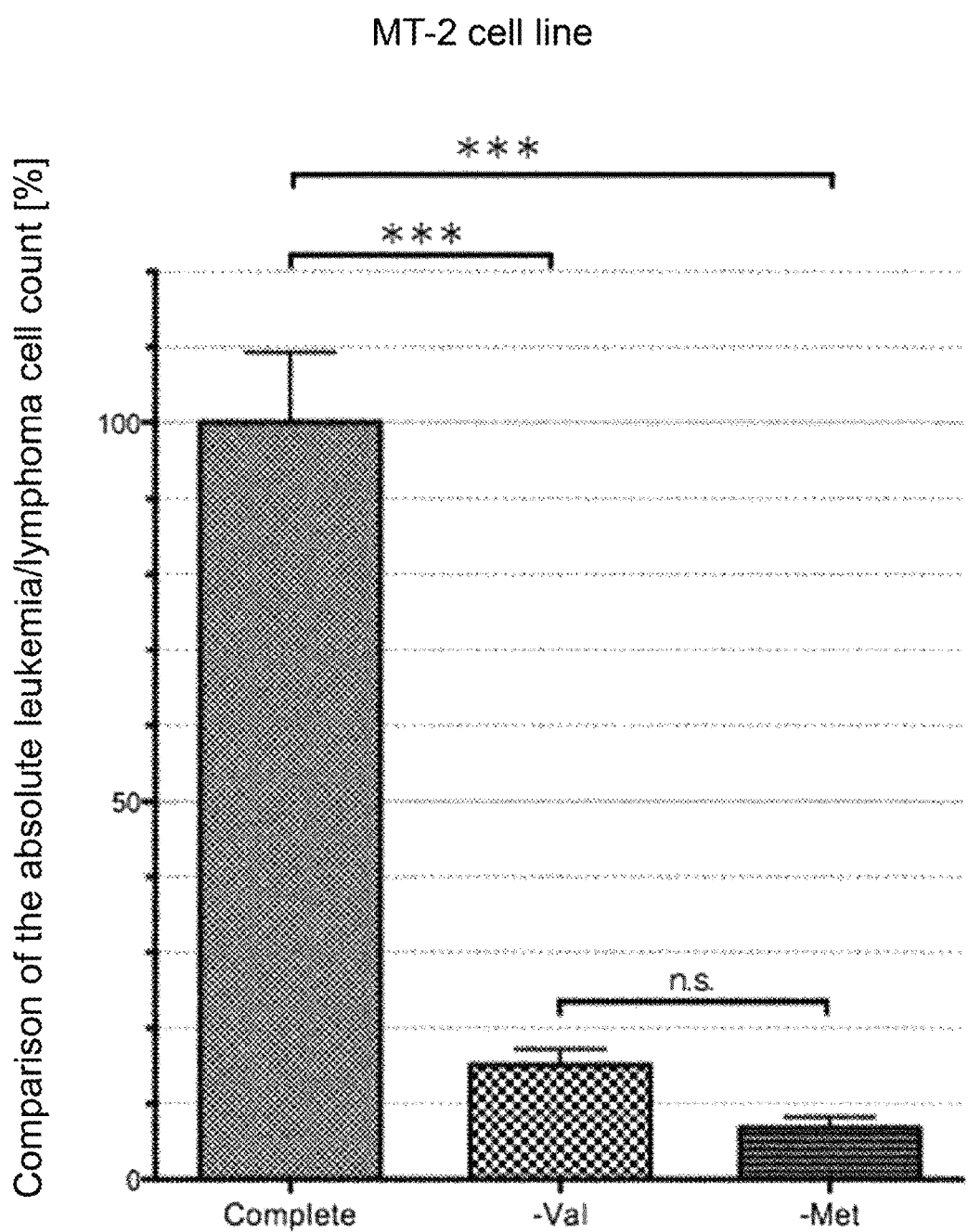

FIG. 6

| Product number | A10021B | | A05080209 | | A05080210 | |
|---|---|---|---|---|---|---|
| | Conventional feed (Complete) | | Valine deficient feed (-Val) | | Methionine deficient feed (-Met) | |
| | [gm%] | [kcal%] | [gm%] | [kcal%] | [gm%] | [kcal%] |
| Protein | 17 | 18 | 16 | 17 | 16 | 17 |
| Carbohydrate | 69 | 71 | 69 | 72 | 69 | 71 |
| Lipid | 5 | 12 | 5 | 12 | 5 | 12 |
| | [gm] | [kcal] | [gm] | [kcal] | [gm] | [kcal] |
| Arginine | 10 | 40 | 10 | 40 | 10 | 40 |
| Histidine HCl · $H_2O$ | 6 | 24 | 6 | 24 | 6 | 24 |
| Isoleucine | 8 | 32 | 8 | 32 | 8 | 32 |
| Leucine | 12 | 48 | 12 | 48 | 12 | 48 |
| Lysine HCl | 14 | 56 | 14 | 56 | 14 | 56 |
| Methionine | 6 | 24 | 6 | 24 | 0 | 0 |
| Phenylalanine | 8 | 32 | 8 | 32 | 8 | 32 |
| Threonine | 8 | 32 | 8 | 32 | 8 | 32 |
| Tryptophan | 2 | 8 | 2 | 8 | 2 | 8 |
| Valine | 8 | 32 | 0 | 0 | 8 | 32 |
| Alanine | 10 | 40 | 10 | 40 | 10 | 40 |
| Asparagine $H_2O$ | 5 | 20 | 5 | 20 | 5 | 20 |
| Aspartic acid | 10 | 40 | 10 | 40 | 10 | 40 |
| Cysteine | 4 | 16 | 4 | 16 | 4 | 16 |
| Glutamic acid | 30 | 120 | 30 | 120 | 30 | 120 |
| Glutamine | 5 | 20 | 5 | 20 | 5 | 20 |
| Glycine | 10 | 40 | 10 | 40 | 10 | 40 |
| Proline | 5 | 20 | 5 | 20 | 5 | 20 |
| Serine | 5 | 20 | 5 | 20 | 5 | 20 |
| Tyrosine | 4 | 16 | 4 | 16 | 4 | 16 |
| Corn starch | 550.5 | 2202 | 558.5 | 2234 | 556.5 | 2226 |
| Maltodextrin 10 | 125 | 500 | 125 | 500 | 125 | 500 |
| Cellulose | 50 | 0 | 50 | 0 | 50 | 0 |
| Corn oil | 50 | 450 | 50 | 450 | 50 | 450 |
| Mineral | 35 | 0 | 35 | 0 | 35 | 0 |
| Sodium bicarbonate | 7.5 | 0 | 7.5 | 0 | 7.5 | 0 |
| Vitamin | 10 | 40 | 10 | 40 | 10 | 40 |
| Choline bitartrate | 2 | 0 | 2 | 0 | 2 | 0 |

Ratio of hematopoietic stem cells

COMPOSITION FOR TREATING ADULT T CELL LEUKEMIA/LYMPHOMA AND METHOD FOR PRODUCING SAME

TECHNICAL FIELD

The present invention relates to a composition for use in treating adult T cell leukemia/lymphoma and a method for producing the same.

BACKGROUND ART

Adult T cell leukemia/lymphoma (ATL) is a hematologic cancer with an extremely poor prognosis, developing in patients infected with HTLV-1 virus. The patient is infected by HTLV-1 mainly at birth by transplacental transmission or through breastmilk, and becomes a HTLV-1 carrier. After a long incubation period of 50 to 60 years on average, only about 5% develop ATL. When the ratio of abnormal lymphocytes (HTLV-1 infected cells) in the peripheral blood exceeds 5%, the patient is diagnosed with ATL. ATL is classified into different stages according to the Shimoyama classification: the smoldering type, the chronic type, the lymphoma type and the acute type, but multiagent chemotherapy (anticancer drug therapy) is conducted for the chronic type, lymphoma type and acute type that are associated with a poor prognosis. Since cell toxicity is enhanced by using multiple anticancer drugs, the side effects are strong and often cause serious anemia (decrease in hemoglobin concentration) or a decrease in platelet count. In addition, ATL cells are resistant to chemotherapy. Recently, an antibody therapy (Mogamulizumab) targeting CCR4, which is an antigen expressed on the cell surface of ATL cells, has also been developed, but the problem is that the effect on the lymph nodes and the spleen is insufficient. There are no known methods that are effective to treat ATL cells of the whole body.

It is known that severe granulocytopenia and anemia develop in mice raised on protein-free feed (Non Patent Literature 1). These abnormalities in the blood cells were reversed with 18% of casein and folic acid (Non Patent Literature 1).

It has been reported that hematopoietic stem cells decrease when valine or cysteine is removed from the nutrition (Patent Literature 1).

CITATION LIST

Patent Literature

Patent Literature 1: WO2016/084850

Non Patent Literature

Non Patent Literature 1: Kornberg A, Daft F S, Sebrell W H, Granulocytopenia and Anemia in Rats Fed Diets of Low Casein Content, Science, 1949, 103(2682):646-8

SUMMARY OF INVENTION

Technical Problem

The present invention provides a composition for use in treating adult T cell leukemia/lymphoma and a method for producing the same.

Solution to Problem

The inventor showed that the growth of HTLV-1 virus infected T cells, ATL cell lines and the patient's ATL cells is inhibited in the absence of valine or methionine, as described in the following examples. The inventor also showed that the growth of ATL is inhibited in model mice grafted with human ATL and nutritionally managed without giving valine or methionine. The inventor further found that no significant impact was observed on the hemoglobin concentration and the platelet count in model mice grafted with human ATL and nutritionally managed without giving valine or methionine. The present invention has been achieved based on such findings.

That is, according to the claimed invention, the following embodiments are provided.

(1) A parenteral nutrition formulation or an enteral nutrition formulation substantially free of valine or methionine, or both.

(2) A composition for use in treating adult T cell leukemia/lymphoma, that contains the nutrition formulations described in (1), and is substantially free of valine or methionine, or both.

(3) A composition for use in treating adult T cell leukemia/lymphoma, that is substantially free of valine or methionine, or both, and that has a composition as a parenteral nutrition formulation or an enteral nutrition formulation except that it is free of valine or methionine, or both.

(4) The composition according to (2) or (3), wherein the subject of administration is a patient with adult T cell leukemia/lymphoma or a patient infected with HTLV-1 virus (5) The composition according to any one of (2) to (4), wherein, except being substantially free of valine or methionine, or both, the parenteral nutrition formulation or the enteral nutrition formulation is designed to be able to provide sufficient nutrients to sustain life for at least three weeks by successive administration.

(6) The composition according to any one of (2) to (5), wherein, except being substantially free of valine or methionine, or both, the parenteral nutrition formulation or the enteral nutrition formulation is designed as a complete nutrition formulation.

(7) The composition according to any one of (2) to (6), for parenteral administration.

(8) A method for detecting a decrease of adult T cell leukemia/lymphoma in the body of a subject suffering from adult T cell leukemia/lymphoma, comprising (a) measuring a number of adult T cell leukemia cells in a peripheral blood sample obtained from the subject before treatment, (b) measuring a number of adult T cell leukemia cells in a peripheral blood sample obtained from the subject during or after treatment, and (c) comparing the cell number found in step (a) with the cell number obtained in step (b), wherein the treatment is substantially free of valine or methionine, or both for the subject for a prescribed time period.

(9) A method for detecting a decrease of HTLV-1 virus infected cells in the body of a subject suffering from adult T cell leukemia/lymphoma or of a subject infected with HTLV-1 virus, comprising (a) measuring a number of HTLV-1 virus infected cells in the peripheral blood sample obtained from the subject before treatment, (b) measuring a number of HTLV-1 virus infected cells in the peripheral blood sample obtained from the subject during or after treatment, and (c) comparing the cell number found in step (a) with the cell number obtained in step (b), wherein the treatment is substantially free of valine or methionine, or both for the subject for a prescribed time period.

(10) The method according to (9), wherein the treatment is conducted by administering the nutritional formulation according to (1) or the composition according to any one of (2) to (7).

(11) The method according to (9), wherein the treatment is a nutrition therapy that is substantially free of valine or methionine, or both for a subject for a prescribed time period.

(12) A method for producing a composition for use in treating adult T cell leukemia/lymphoma, comprising mixing the essential nutrients to the body in such a way that the composition is substantially free of valine or methionine, or both.

(13) The method according to (12), wherein the nutrients are at least sugars, essential amino acids, vitamins and essential trace elements.

(14) The method according to (12), wherein the composition contains nutrients in sufficient amount to sustain life for at least three weeks by successive administration.

(15) Use of nutrients for producing a pharmaceutical composition for use in treating adult T cell leukemia/lymphoma, wherein the nutrients are any nutrient other than valine or methionine, or both.

(16) A pharmaceutical composition for use in treating adult T cell leukemia/lymphoma in a subject, containing a therapeutic agent for adult T cell leukemia/lymphoma, wherein the subject is nutritionally managed, or scheduled to be nutritionally managed by a diet free of valine or methionine, or both.

According to the present invention, ATL can be treated in subjects (for example, humans) by providing a diet free of valine or methionine, or both.

BRIEF DESCRIPTION OF DRAWINGS

FIG. 1 shows the amino acid contents of a conventional culture medium (Complete), a culture medium free of valine (−Val) and a culture medium free of methionine (−Met) that are used in the examples.

FIG. 2 shows the impact of the culture conditions free of valine or methionine on the proliferation of HTLV-1 virus infected cell lines.

FIG. 6 shows the component content of conventional feed (Complete), feed free of valine (−Val) and feed free of methionine (−Met), respectively, that are used in the examples.

DETAILED DESCRIPTION OF INVENTION

Figure 3:
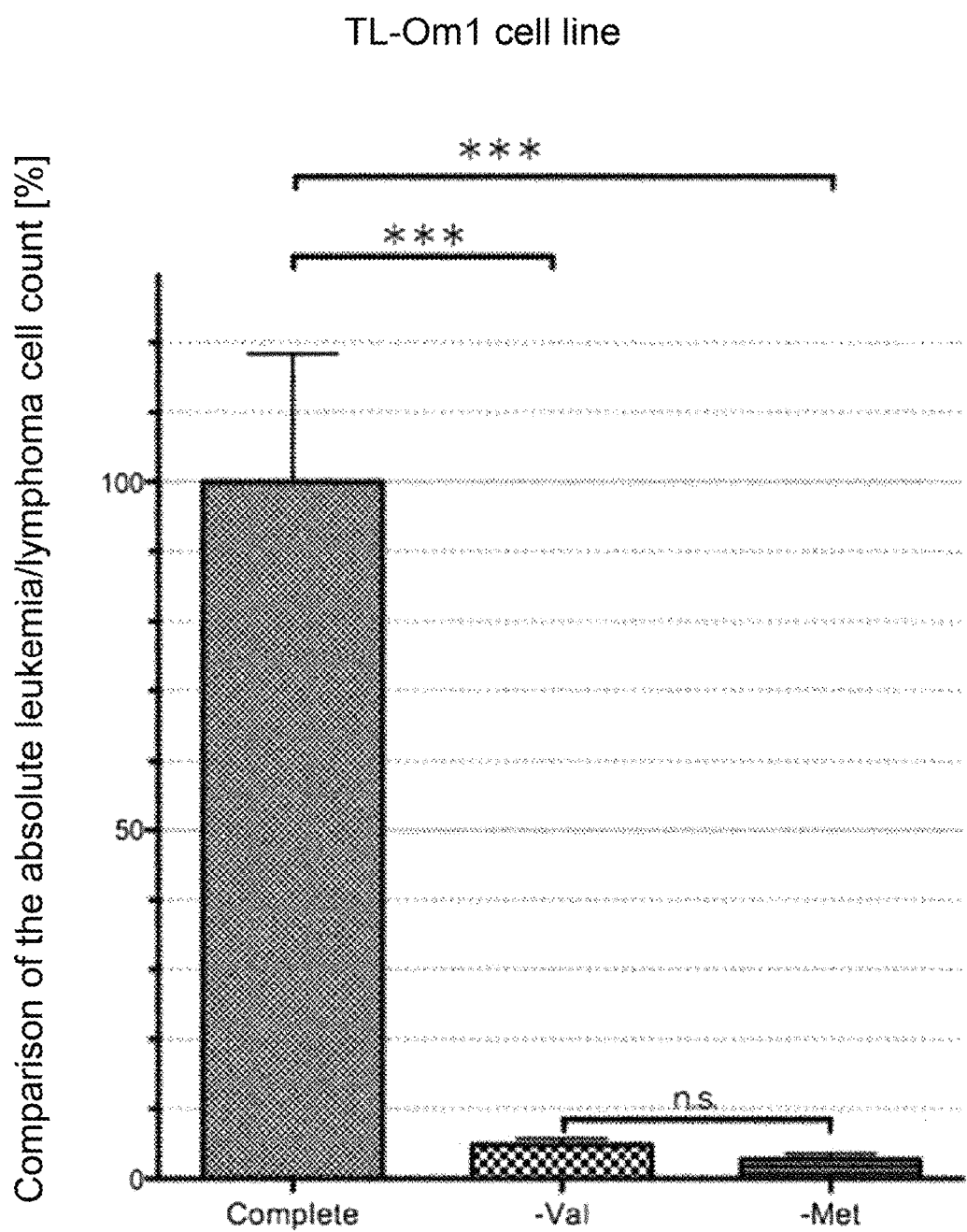
FIG. 3 shows the impact of the culture conditions free of valine or methionine on the proliferation of ATL cell lines.

In the present description, "subject" means an animal, preferably a mammal, especially a human.

In the present description, "adult T cell leukemia/lymphoma" (hereinafter sometimes simply referred to as "ATL") is a leukemia/lymphoma caused by infection of human T cell leukemia virus type 1 (HTLV-1). ATL is also sometimes called "adult T cell leukemia" or "adult T cell lymphoma". Generally, when the ratio of abnormal lymphocytes in the peripheral blood exceeds 5%, the subject is diagnosed with ATL, but in the present description, "ATL cell" means a HTLV-1 infected cell proliferating monoclonally in the body of a patient who has developed ATL.

In the present description, a "HTLV-1 carrier" means a subject (a warm-blooded animal, especially a human) infected with HTLV-1 virus. When a subject has antibodies against HTLV-1, the subject can be regarded as a HTLV-1 carrier.

In the present description, the meaning of a "treatment" and its derivatives also includes therapy and prophylaxis. Moreover, the meaning of a "treatment" also includes the suppression of organ invasion.

In the present description, "prophylaxis" and its derivatives mean to decrease the incidence of ATL in HTLV-1 carriers before developing ATL.

In the present description, "therapy" and its derivatives means the remission, relief and/or delay of aggravation of the clinical symptoms of ATL in subjects having developed ATL.

In the present description, the meaning of "comprise" or "comprising" also includes "consist of" or "consist only of".

Therefore, in the present description, "treat ATL" and its derivatives include both therapy of ATL and prophylaxis of ATL. Therefore, in the present description, "composition for use in treating ATL" is used to mean both "composition for use in therapy of ATL" and "composition for use in prophylaxis of ATL in HTLV-1 carriers". The rationale behind this is that, since it decreases ATL cells and decreases HTLV-1 virus infected T cells, "composition for use in treating ATL" can be also read as "composition for use in decreasing ATL cells" and "composition for use in decreasing HTLV-1 virus infected T cells".

As described in the following examples, the inventor has found that ATL cells in the body of animals can be decreased when sustaining the animals without valine or methionine. Therefore, the present invention provides a method to decrease ATL cells or HTLV-1 virus infected T cells in the body of animals by sustaining the animals without valine or methionine, or both, as well as a composition free of valine or methionine, or both to be used in the method.

ATL can be diagnosed by a doctor from the clinical symptoms of a subject. For example, the patient who has more than 5% of abnormal lymphocytes (HTLV-1 infected cells) in the peripheral blood can be diagnosed with ATL. Moreover, ATL is a disease caused by the monoclonal proliferation of T cells wherein HTLV-1 has been integrated as a provirus in the genome, and it can be diagnosed by detecting by a Southern blot method or by Polymerase chain reaction (PCR) that the HTLV-1 provirus is integrated monoclonally in the DNA of the ATL cells in the sample obtained from the subject.

The particle agglutination method (PA method), the chemiluminescence method, the indirect fluorescent antibody method with the virus infected cells as antigen, and the Western blot method are known as test methods for diagnosing that a subject is a HTLV-1 carrier, and can be used appropriately. In the Western blot method, if, in the sample obtained from the subject, the antibody to the envelope protein of the virus (gp46) is positive, and one or more antibodies against the three core proteins (p19, p24 and p53) are positive, the subject can be diagnosed as a HTLV-1 carrier. Or, the subject may supplementary be diagnosed as a carrier by a polymerase chain reaction (PCR) that auxilarily amplifies the provirus genome of HTLV-1.

HTLV-1 virus infected T cells can be detected as CD4 and CADM1 (Cell Adhesion Molecule 1) positive cells by immunostaining or flow cytometry. Moreover, their clonality can be determined by using the repertoire diversity of T cell receptors (TCR) or the genome integration position of the HTLV-1 provirus, and if monoclonal, the cells detected can be identified as ATL cells.

According to the present invention, the nutrition of a subject can be managed such that no valine or no methionine, or both will be provide to a subject. This allows to decrease ATL cells and HTLV-1 virus infected T cells in the body of the subject, that is, to treat ATL.

In one aspect, the composition for use in treating ATL contains a parenteral nutrition formulation or an enteral nutrition formulation, but it is a composition substantially free of valine or methionine, or both.

In the present description, "free of valine" is used interchangeably with "lacking valine". In the present description, "free of valine" means it is also free of valine in the constituent peptides.

In the present description, "free of methionine" is used interchangeably with "lacking methionine". In the present description, "free of methionine" means it is also free of methionine in the constituent peptides.

In the present description, "substantially" means that there may be contamination to a degree that cannot be avoided during the production process.

As used herein, "parenteral nutrition formulation" means a nutrition formulation used for parenteral nutrition methods. Examples of parenteral nutrition formulations include peripheral parenteral nutrition formulations that administer nutrients in a peripheral vein, and central venous nutrition formulations that administer nutrients in a central vein. Usually, if the bowel is functioning, enteral nutrition is selected as the nutrition method and an enteral nutrition formulation is administered to the subject, but if enteral nutrition is difficult, parenteral nutrition is selected and a Parenteral nutrition formulation is administered to the subject. Examples of parenteral nutrition formulations include peripheral parenteral nutrition formulations and central venous nutrition formulations. Parenteral nutrition formulations are usually transfusion formulations or aqueous solutions containing sugars, electrolytes and amino acids, and may further contain vitamins. Central venous nutrition formulations usual contain vitamins and trace elements necessary to the organism (for example, vitamin supplements for transfusion, multivitamin supplements for transfusion and trace element preparations for transfusion), in addition to the sugars, electrolytes and amino acids.

As used herein, "enteral nutrition formulation" means a nutrition formulation used for enteral nutrition methods. Examples of enteral nutrition formulations include polymeric formulas, oligomeric formulas and elemental diets. Polymeric formulas contain proteins as a nitrogen source, oligomeric formulas contain low molecular peptides and amino acids as a nitrogen source, and elemental diets contain amino acids as a nitrogen source. In the present invention, elemental diets can be used preferably as an enteral nutrition formulation.

In the present description, "to have a composition as a parenteral nutrition formulation or an enteral nutrition formulation except for valine" means that the composition other than valine is the same as a parenteral nutrition formulation or an enteral nutrition formulation, or that the composition other than valine is analogous, and functions as a parenteral nutrition formulation or an enteral nutrition formulation.

In the present description, "to have a composition as a parenteral nutrition formulation or an enteral nutrition formulation except for methionine" means that the composition other than methionine is the same as a parenteral nutrition formulation or an enteral nutrition formulation, or that the composition other than methionine is analogous, and functions as a parenteral nutrition formulation or an enteral nutrition formulation.

In the present description, "designed as a complete nutrition formulation, except that it is substantially free of valine" means that it has the composition of a nutrition formulation designed as a complete nutrition formulation, but that it is free of valine in its composition. Namely, in a composition that is "designed as a complete nutrition formulation, except that it is substantially free of valine", the composition except valine can be the same as a complete nutrition formulation.

In the present description, "to be designed as a complete nutrition formulation, except that it is substantially free of methionine" means that it has the composition of a nutrition formulation designed as a complete nutrition formulation, but that it is free of methionine in its composition. Namely, in a composition that is "designed as a complete nutrition formulation, except that it is substantially free of methionine", the composition except methionine can be the same as a complete nutrition formulation.

In the present description, "designed to provide sufficient nutrients to sustain life for at least three weeks by successive administration, except that it is substantially free of valine" or similar expressions mean that it has the composition of a nutrition formulation designed to provide sufficient nutrients to sustain life for at least three weeks by successive administration, but that it is free of valine in its composition.

In the present description, "designed to provide sufficient nutrients to sustain life for at least three weeks by successive administration, except that it is substantially free of methionine" or similar expressions mean that it has the composition of a nutrition formulation designed to provide sufficient nutrients to sustain life for at least three weeks by successive administration, but that it is free of methionine in its composition.

A parenteral nutrition method or an enteral nutrition method is sometimes selected as a nutrition management method so that the nutrition management of a subject is medically appropriate. The above parenteral nutrition formulations and enteral nutrition formulations are commercially available for this kind of appropriate nutrition management. In the parenteral nutrition method or the enteral nutrition method, a formulation to increase the energy intake such as a fat emulsion may be used in addition to the above parenteral nutrition formulations or enteral nutrition formulations. The fat emulsion is administered with a nutrition formulation to provide energy or to prevent a fatty acid deficiency, it generally contains an emulsion of fatty acid, the fatty acid can be for example derived from soybean oil and the emulsifier can be lecithin derived from yolk. However, in either case, the nutrition is managed so that valine or methionine, or both is substantially not ingested by the subject.

Since ATL cells and HTLV-1 virus infected T cells can be decreased in the body of subject animals by sustaining the animals without valine, the present invention can be preferably used so that the parenteral nutrition formulation or the enteral nutrition formulation substantially free of valine decrease ATL cells or HTLV-1 virus infected T cells, or to treat ATL.

Since ATL cells and HTLV-1 virus infected T cells can be decreased in the body of subject animals by sustaining animals without methionine, the present invention can be preferably used so that the parenteral nutrition formulation or the enteral nutrition formulation substantially free of methionine decrease ATL cells or HTLV-1 virus infected T cells, or to treat ATL.

Moreover, parenteral nutrition formulations or enteral nutrition formulations substantially free of valine and methionine can be preferably used to decrease ATL cells or HTLV-1 virus infected T cells, or to treat ATL.

In one aspect, the composition for use in treating ATL of the present invention contains all of the twenty amino acids except valine. In one aspect, the composition for use in treating ATL of the present invention is substantially free of peptide containing valine. Moreover, in one aspect, the composition for use in treating ATL of the present invention contains all of the twenty amino acids except valine, and further contains sugars, electrolytes, vitamins and essential trace elements. In one aspect, the composition for use in treating ATL of the present invention contains all of the twenty amino acids except valine, and further contains sugars, electrolytes, vitamins and essential trace elements; and is used in combination with a fat emulsion. The amount of each component contained in the composition for use in treating ATL of the present invention can be the same as the amount of each component contained in conventional parenteral nutrition formulations or enteral nutrition formulations.

In one aspect, the composition for use in treating ATL of the present invention contains all of the twenty amino acids except methionine. In one aspect, the composition for use in treating ATL of the present invention is substantially free of peptide containing methionine. Moreover, in one aspect, the composition for use in treating ATL of the present invention contains all of the twenty amino acids except methionine, and further contains sugars, electrolytes, vitamins and essential trace elements. In one aspect, the composition for use in treating ATL of the present invention contains all of the twenty amino acids except methionine, and further contains sugars, electrolytes, vitamins and essential trace elements; and is used in combination with a fat emulsion. The amount of each component contained in the composition for use in treating ATL of the present invention can be the same as the amount of each component contained in conventional parenteral nutrition formulations or enteral nutrition formulations.

In one aspect, the composition for use in treating ATL of the present invention contains all of the twenty amino acids except valine and methionine. In one aspect, the composition for use in treating ATL of the present invention is substantially free of peptide containing valine or methionine. Moreover, in one aspect, the composition for use in treating ATL of the present invention contains all of the twenty amino acids except valine and methionine, and further contains sugars, electrolytes, vitamins and essential trace elements. In one aspect, the composition for use in treating ATL of the present invention contains all of the twenty amino acids except valine and methionine, and further contains sugars, electrolytes, vitamins and essential trace elements; and is used in combination with a fat emulsion. The amount of each component contained in the composition for use in treating ATL of the present invention can be the same as the amount of each component contained in normal parenteral nutrition formulations or enteral nutrition formulations.

In a pharmaceutical composition for parenteral administration, each nutrient consists of components pharmaceutically acceptable.

In one aspect of the present invention, the subject to be administered the composition of the present invention is a subject with ATL or a subject infected with HTLV-1 virus.

A parenteral nutrition formulation or enteral nutrition formulation substantially free of valine can be obtained by mixing a formulation of amino acids other than valine as amino acid with the other constituents (sugars, electrolytes, etc.) of the nutrition formulation.

A parenteral nutrition formulation or enteral nutrition formulation substantially free of methionine can be obtained by mixing a formulation of amino acids other than methionine as amino acid with the other constituents (sugars, electrolytes, etc.) of the nutrition formulation.

A parenteral nutrition formulation or enteral nutrition formulation substantially free of valine and methionine can be obtained by mixing a formulation of amino acids other than valine and methionine as amino acid with the other constituents (sugars, electrolytes, etc.) of the nutrition formulation.

The composition for use in treating ATL of the present invention should be designed to provide sufficient nutrients to sustain life for at least three weeks by successive administration, and preferably, can be designed to provide sufficient nutrients to sustain life for four or five weeks or more.

According to the present invention, when providing nutrition to the subject without substantially providing valine or methionine, ATL cells and HTLV-1 virus infected T cells in the body of a subject decreases. Therefore, according to the present invention, provided is a method for decreasing ATL cells and HTLV-1 virus infected T cells in the body of a subject, comprising managing the nutrition (administer nutrition) without substantially providing valine or methionine, or both to the subject. The nutrition can be managed by an enteral nutrition method or a parenteral nutrition method. The nutrition may be managed by administering the above enteral nutrition formulations or parenteral nutrition formulations to a subject.

According to the present invention, provided is a method for detecting a decrease of ATL cells or HTLV-1 virus infected T cells in the body of a subject suffering from adult T cell leukemia/lymphoma, comprising (a) measuring a number of ATL cells or HTLV-1 virus infected T cells in a peripheral blood sample obtained from the subject before treatment, (b) measuring a number of ATL cells or HTLV-1 virus infected T cells in a peripheral blood sample obtained from the subject during or after treatment, and (c) comparing the cell number found in step (a) with the cell number obtained in step (b), wherein the treatment is substantially free of valine or methionine, or both for the subject for a prescribed time period. In this method, when, in step (c), the cell number obtained in step (b) is less than the cell number found in step (a), it can be considered that ATL cells or HTLV-1 virus infected T cells in the body has decreased. In one aspect, the treatment is a nutrition therapy by an enteral nutrition method or a parenteral nutrition method. In one aspect, the treatment may be conducted by administering the above enteral nutrition formulation or parenteral nutrition formulation to the subject.

According to the present invention, provided is a method for detecting a decrease of HTLV-1 virus infected cells in the body of a subject infected with HTLV-1 virus, comprising (a) measuring a number of HTLV-1 virus infected cells in a peripheral blood sample obtained from the subject before treatment, (b) measuring a number of HTLV-1 virus infected cells in a peripheral blood sample obtained from this subject during or after treatment, and (c) comparing the cell number found in step (a) with the cell number obtained in step (b), wherein the treatment is substantially free of valine or methionine, or both for the subject for a prescribed time period. In this method, when, in step (c), the cell number obtained in step (b) is less than the cell number found in step (a), it can be considered that HTLV-1 virus infected cells in the body has decreased. In one aspect, the treatment is a nutrition therapy by an enteral nutrition method or a parenteral nutrition method. In one aspect, the treatment may be conducted by administering the above enteral nutrition formulation or parenteral nutrition formulation to the subject.

In the method for detecting a decrease of ATL cells or HTLV-1 virus infected cells in the body of a subject of the present invention, the prescribed time period is preferably 1 day or more, 2 days or more, 3 days or more, 4 days or more, 5 days or more, 6 days or more, 1 week or more, 2 weeks or more, 3 weeks or more, or 4 weeks or more, and cannot be a time period so long that the patient dies. In one aspect of the present invention, the prescribed time period is 1 day to 5 weeks, 1 to 4 weeks, or 2 to 3 weeks.

In the method for detecting a decrease of ATL cells or HTLV-1 virus infected cells in the body of a subject of the present invention, the subject can be a mammal, preferably a human. In one aspect of the present invention, the subject is an ATL patient. In one aspect of the present invention, the subject is a subject infected with HTLV-1.

According to the present invention, provided is a method for producing a composition for use in decreasing ATL cells or HTLV-1 virus infected cells, or for use in treating ATL, that includes mixing nutrients without substantially incorporating valine or methionine, or both in the composition. The nutrients that are mixed can be sugars, amino acids, vitamins, electrolytes and essential trace elements. In one aspect, the amino acid that is mixed is at least one amino acid selected from the essential amino acids such as tryptophan, lysine, phenylalanine, threonine, leucine, isoleucine and histidine, or all the amino acids. The composition administered by a parenteral nutrition method consists of components pharmaceutically acceptable.

Examples of trace elements necessary to the body include iron, zinc, copper, selenium, chromium, cobalt, iodine, manganese and molybdenum. The amount of essential trace elements administered is approximately as follows.

Iron: 20 to 200 µg/kg body weight/day
Zinc: 40 to 60 µg/kg body weight/day
Copper: 20 to 50 µg/kg body weight/day
Selenium: 2 to 7 µg/kg body weight/day
Chromium: 0.1 to 0.2 µg/kg body weight/day
Iodine: 1 to 15 µg/kg body weight/day
Manganese: 1 to 60 µg/kg body weight/day
Molybdenum: 0.1 to 0.5 µg/kg body weight/day Therefore, the essential trace elements can be mixed in the composition of the present invention with the above necessary amounts as a guide.

According to the present invention, provided is a method for treating AIL in a patient in need thereof, comprising sustaining the life of the patients without substantially providing valine to the subject (or by providing the other nutrients), thereby decreasing ATL cells or HTLV-1 virus infected cells in the body of the patient. The method for treating ATL of the present invention may be conducted before or in the middle of other therapies, for example, antibody therapy, immune therapy, radiation therapy, hematopoietic stem cell transplant therapy, or the therapy with anticancer drugs for use in treating ATL. The method for treating ATL of the present invention may further include providing substantially no valine to the subject until the ATL cells or the HTLV-1 virus infected cells of the patient are substantially removed.

According to the present invention, provided is a method for treating ATL in a patient in need thereof, comprising sustaining the life of the patients without substantially providing methionine to the subject (or by providing the other nutrients), thereby decreasing ATL cells or HTLV-1 virus infected cells in the body of the patient. The method for treating ATL of the present invention may be conducted before or in the middle of other therapies, for example, antibody therapy, immune therapy, radiation therapy, hemopoietic stem cell transplant therapy, or the therapy with anticancer drugs for use in treating ATL. The method for treating ATL of the present invention may further include providing substantially no methionine to the subject until the ATL cells or the HTLV-1 virus infected cells of the patient are substantially removed.

According to the present invention, provided is a method for treating ATL in a patient in need thereof, comprising sustaining the life of the patients by providing substantially no valine and no methionine to the subject (or by providing the other nutrients), thereby decreasing ATL cells or HTLV-1 virus infected cells in the body of the patient. The method for treating ATL of the present invention may be conducted before or in the middle of other therapies, for example, antibody therapy, immune therapy, radiation therapy, hemopoietic stem c transplant therapy, or the therapy with anticancer drugs for use in treating ATL. The method for treating ATL of the present invention may further include providing substantially no valine and no methionine to the subject until the ATL cells or the HTLV-1 virus infected cells of the patient are substantially removed.

The inventor has found that the number of hematopoietic stem cells decreases in the subject when providing no valine to the subject. Namely, by managing his nutrition for a prescribed time period by providing no valine, an ATL patient can avoid excess administration of anticancer drugs (in some cases, can completely avoid the administration of anticancer drugs), and can reduce the intensity of the chemotherapy or radiation therapy that has been conventionally given to decrease hematopoietic stem cells, or completely avoid chemotherapy or radiation therapy, and significantly reduce the side effects of the treatment. Therefore, the method for treating ATL of the present invention may further include transplanting hematopoietic stem cells to the subject after treatment (optionally with no need to use other methods for decreasing the number of hematopoietic stem cells). Or, the method for treating ATL of the present invention can be conducted as a pre-treatment (or as a method to replace the pre-treatment) in an ATL patient receiving a hematopoietic stem cell transplant. Moreover, the composition or nutrition formulation of the present invention can be administered to an ATL patient receiving a hematopoietic stem cell transplant, thereby decreasing ATL cells in the body of the ATL patient, and decreasing the number of hematopoietic stem cells. Therefore, the method for treating ATL, or the composition or nutrition formulation, of the present invention can be conducted or used in the ATL patient receiving a hematopoietic stem cell transplant for treating ATL, and/or for decreasing hematopoietic stem cells.

Therefore, the composition or nutrition formulation of the present invention can be a composition or a nutrition formulation for use in administration to an ATL patient receiving a hematopoietic stem cell transplant. In the method of the present invention, a method for treating ATL in the ATL patient comprising managing the nutrition of the patient for a prescribed time period (for example, 3 weeks or more, 4 weeks or more) by providing no valine, then measuring the number of hematopoietic stem cells in the body of the patient, and transplanting hematopoietic stem cells in the body of the patient after that the number of the hematopoietic stem cells has sufficiently decreased (wherein the ATL patient optionally need not receive other pre-treatments for decreasing hematopoietic stem cells in the body of a patient when transplanting hematopoietic stem cells) is also provided.

According to the present invention, provided is a pharmaceutical composition for use in treating adult T cell leukemia/lymphoma in a subject, that contains a therapeutic agent for adult T cell leukemia/lymphoma, and where the subject is nutritionally managed by a diet free of valine or methionine, or both. In one aspect, for the above pharmaceutical composition, the subject is a subject who is nutritionally managed for a time period of 1, 2 or 3 weeks or more, or a subject scheduled to be nutritionally managed for a time period of 1, 2 or 3 weeks or more by a diet free of valine or methionine, or both. This aspect is a combination therapy of a therapeutic agent for adult T cell leukemia/lymphoma and the method for treating ATL of the present invention.

The present invention relates to use of nutrients for producing a composition for use in decreasing ATL cells or HTLV-1 virus infected cells, or a composition for use in treating ATL, wherein the nutrients are any nutrient other than valine or methionine, or both. The nutrients that are used can be sugars, amino acids, vitamins, electrolytes and essential trace elements.

The present invention relates to use of nutrients for producing a composition for use in decreasing ATL cells or HTLV-1 virus infected cells, or a composition for use in treating ATL, wherein the nutrients are any nutrient other than valine. The nutrients that are used can be sugars, amino acids, vitamins, electrolytes and essential trace elements.

In one aspect, the amino acid that is used is at least one amino acid selected from the essential amino acids such as tryptophan, lysine, methionine, phenylalanine, threonine, leucine, isoleucine and histidine, or all the amino acids selected from the above essential amino acids. In one aspect, the nutrients include all the amino acids except valine as amino acid.

The present invention relates to a use of nutrients for producing a composition for use in decreasing ATL cells or HTLV-1 virus infected cells, or a composition for use in treating ATL, wherein the nutrients are any nutrient other than methionine. The nutrients that are used can be sugars, amino acids, vitamins, electrolytes and essential trace elements.

In one aspect, the amino acid that is used is at least one amino acid selected from the essential amino acids such as valine, tryptophan, lysine, phenylalanine, threonine, leucine, isoleucine and histidine, or all the amino acids selected from the above essential amino acids. In one aspect, the nutrients include all the amino acids except methionine as amino acid.

The present invention relates to a use of nutrients for producing a composition for use in decreasing ATL cells or HTLV-1 virus infected cells, or a composition for use in treating ATL, wherein the nutrients are any nutrient other than valine and methionine. The nutrients that are used can be sugars, amino acids, vitamins, electrolytes and essential trace elements.

In one aspect, the amino acid that is used is at least one amino acid selected from the essential amino acids such as tryptophan, lysine, phenylalanine, threonine, leucine, isoleucine and histidine, or all the amino acids selected from the above essential amino acids. In one aspect, the nutrients include all the amino acids except valine and methionine as amino acid.

In one aspect, the amino acids that are used are all the amino acids (excluding valine). Therefore, in one aspect, the nutrients that are used are sugars, amino acids, vitamins, electrolytes and essential trace elements, and the amino acid is at least one amino acid selected from the essential amino acids such as tryptophan, lysine, phenylalanine, threonine, leucine, isoleucine and histidine, or all the amino acids selected from the above essential amino acids.

In one aspect, the amino acids that are used are all the amino acids (excluding methionine). Therefore, in one aspect, the nutrients that are used are sugars, amino acids, vitamins, electrolytes and essential trace elements, and the amino acid is at least one amino acid selected from the essential amino acids such as tryptophan, lysine, valine, phenylalanine, threonine, leucine, isoleucine and histidine, or all the amino acids selected from the above essential amino acids.

In one aspect, the amino acids that are used are all the amino acids (excluding valine and methionine). Therefore, in one aspect, the nutrients that are used are sugars, amino acids, vitamins, electrolytes and essential trace elements, and the amino acid is at least one amino acid selected from the essential amino acids such as tryptophan, lysine, phenylalanine, threonine, leucine, isoleucine and histidine, or all the amino acids selected from the above essential amino acids.

In one aspect, the nutrients that are used are sugars, amino acids, vitamins, electrolytes and essential trace elements, and the amino acids are asparagine, aspartic acid, serine, threonine, glutamine, glutamic acid, proline, glycine, methionine, leucine, isoleucine, tyrosine, phenylalanine, histidine, alanine, lysine, tryptophan and arginine.

In one aspect, the nutrients that are used are sugars, amino acids, vitamins, electrolytes and essential trace elements, and the amino acids are asparagine, aspartic acid, serine, threonine, glutamine, glutamic acid, proline, glycine, valine, leucine, isoleucine, tyrosine, phenylalanine, histidine, alanine, lysine, tryptophan and arginine.

In one aspect, the nutrients that are used are sugars, amino acids, vitamins, electrolytes and essential trace elements, and the amino acids are asparagine, aspartic acid, serine, threonine, glutamine, glutamic acid, proline, glycine, leucine, isoleucine, tyrosine, phenylalanine, histidine, alanine, lysine, tryptophan and arginine.

In one aspect, the nutrients that are used are sugars, amino acids, vitamins, electrolytes and essential trace elements, and the amino acids are asparagine, aspartic acid, serine, threonine, glutamine, glutamic acid, proline, glycine, methionine, leucine, isoleucine, tyrosine, phenylalanine, histidine, alanine, lysine, tryptophan, cysteine and arginine.

In one aspect, the nutrients that are used are sugars, amino acids, vitamins, electrolytes and essential trace elements, and the amino acids are asparagine, aspartic acid, serine, threonine, glutamine, glutamic acid, proline, glycine, valine, leucine, isoleucine, tyrosine, phenylalanine, histidine, alanine, lysine, tryptophan, cysteine and arginine.

In one aspect, the nutrients that are used are sugars, amino acids, vitamins, electrolytes and essential trace elements, and the amino acids are asparagine, aspartic acid, serine, threonine, glutamine, glutamic acid, proline, glycine, leucine, isoleucine, tyrosine, phenylalanine, histidine, alanine, lysine, tryptophan, cysteine and arginine.

The content of each nutrient that is used can be determined appropriately by a person skilled in the art according to the subject of administration. For example, the content of each nutrient that is used can be the same as the content of each nutrient in a parenteral nutrition formulation or an enteral nutrition formulation.

EXAMPLES

Example 1

The Effect on Cell Proliferation of an Amino Acid Deficiency in a Cell Culture Medium The impact on cell proliferation by the lack of each amino acid was examined by preparing a cell culture medium which lacks one of the twenty amino acids.

As cells, HTLV-1 infected T cell lines (MT-2), adult T cell leukemia cell lines (TL-Om1), and subcultured ATL cells from acute ATL patients were examined. The subcultured ATL cells from acute ATL patients were obtained by subculturing after purifying only ATL cells from a human patient specimen diagnosed with acute ATL using flow cytometry sorting, and by confirming they were monoclonal.

As culture media, DMEM/F12 culture medium (referred to as "conventional"), valine deficient culture medium (−Val) and methionine deficient culture medium (−Met) shown in FIG. 1 were used. All culture media were used under the serum-free conditions. Moreover, bovine serum albumin was added to all culture media so that the final concentration be 0.5 weight/volume %.

(1) Effect on the Proliferation of HTLV-1 Infected Cells

HTLV-1 infected T cell lines (MT-2) were cultured in the culture media described in FIG. 1 and the cell number was measured after two weeks. The cell numbers when using a valine deficient culture medium (−Val) and a methionine deficient culture medium (−Met) were each shown by a relative value, with the cell number when using a conventional culture medium (Complete) as 100%. The results were as shown in FIG. 2.

As shown in FIG. 2, in culture media deficient in either valine or methionine, the proliferation of HTLV-1 infected T cell lines (MT-2) was found to be significantly inhibited.

Adult T cell leukemia is known to develop from a part of humans infected with HTLV-1 (also referred to as carrier). The results of the present example suggest that, by removing valine or methionine from the diet, the proliferation of HTLV-1 infected cells can be inhibited in carriers before the onset, that is, it can prevent adult T cell leukemia.

(2) Effect on the Proliferation of Adult T Cell Leukemia Cell Lines and Subcultured ATL Cells from Acute ATL Patients Adult T cell leukemia roll lines (TL-Om1), and subcultured ATL cells from acute ATL patients were cultured with mesenchymal cells (MS-5) for two weeks in a culture medium of the composition shown in FIG. 1. The cell numbers when using a valine deficient culture medium (−Val) and a methionine deficient culture medium (−Met) were each shown by a relative value, with the cell number when using a conventional culture medium (Complete) as 100%. The results were as shown in FIGS. 3, 4A and 4B.

As shown in FIG. 3, in culture media deficient in either valine or methionine, the proliferation of adult T cell leukemia cell lines (TL-Om1) was found to be significantly inhibited.

Figure 4A:
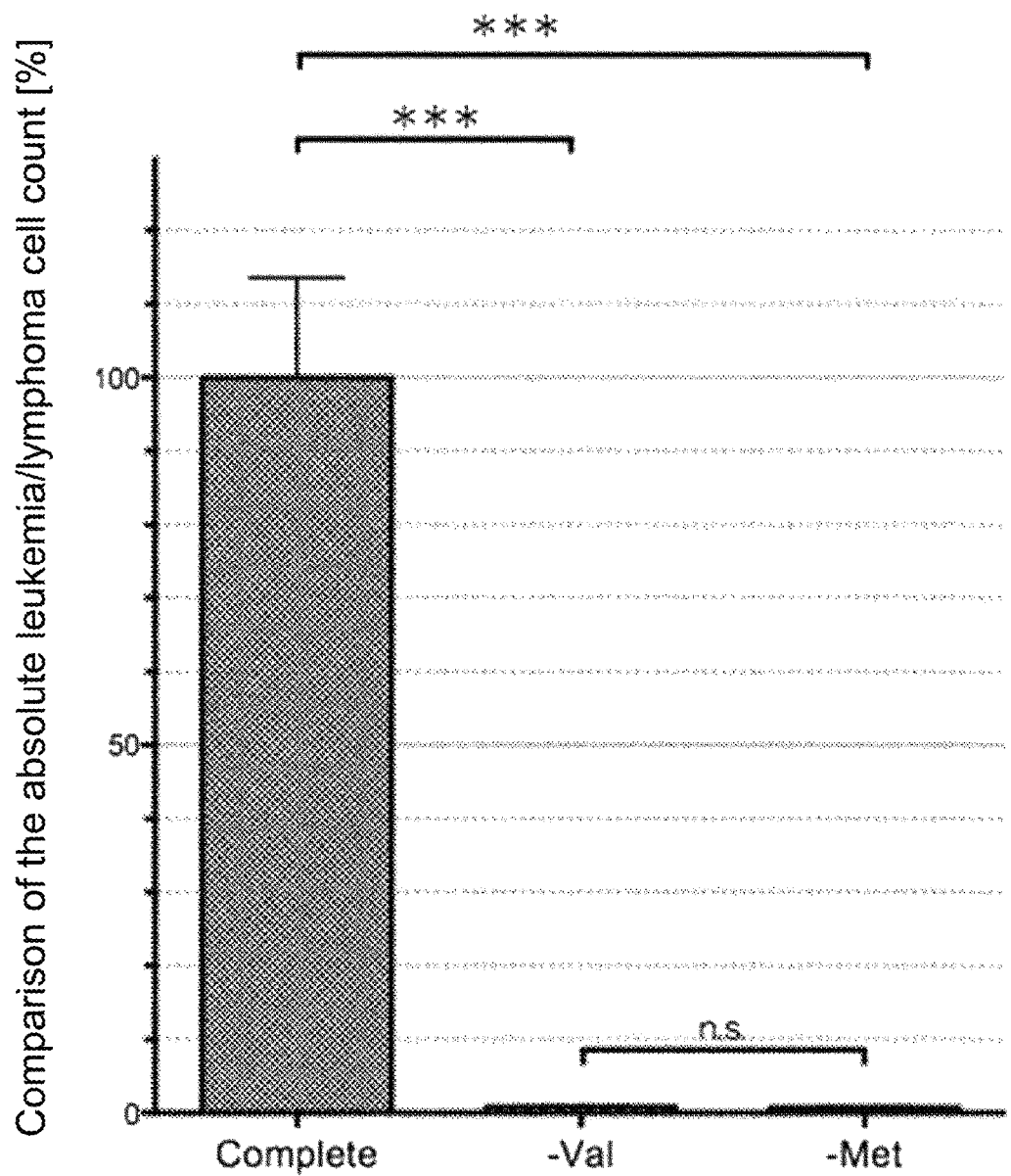
FIG. 4A shows the impact of the culture conditions free of valine or methionine on the proliferation of subcultured ATL cells from acute ATL patients.
Figure 4B:
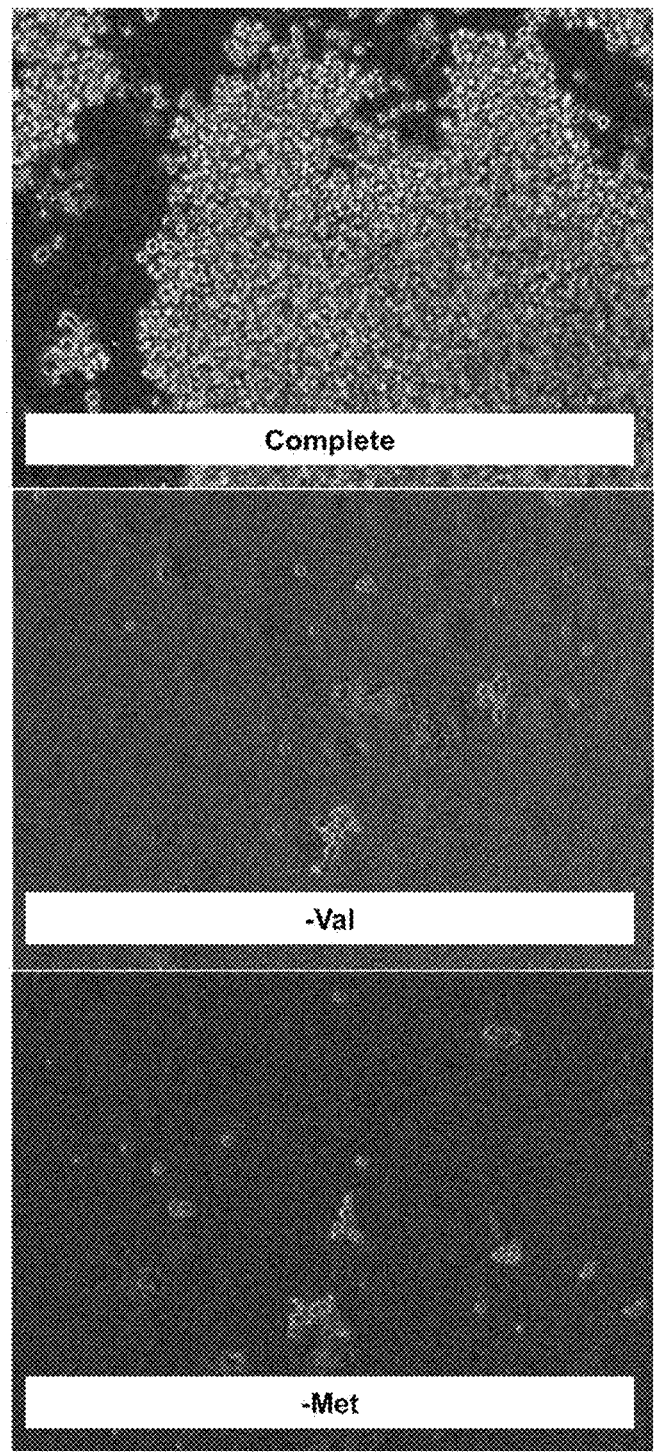
FIG. 4B shows a micrograph by inverted micrography showing the impact of the culture conditions free of valine or methionine on the proliferation of subcultured ATL cells from acute ATL patients.

Moreover, as shown in FIG. 4A, in culture media deficient in either valine or methionine, the proliferation of subcultured ATL cells from acute ATL patients was also found to be significantly inhibited. FIG. 4B shows a micrograph of subcultured ATL cells from acute ATL patients after 2 weeks cultivation. Compared to when using a conventional culture medium, it was also visually clear that the cell number was significantly smaller in culture media deficient in either valine or methionine.

Figure 5:
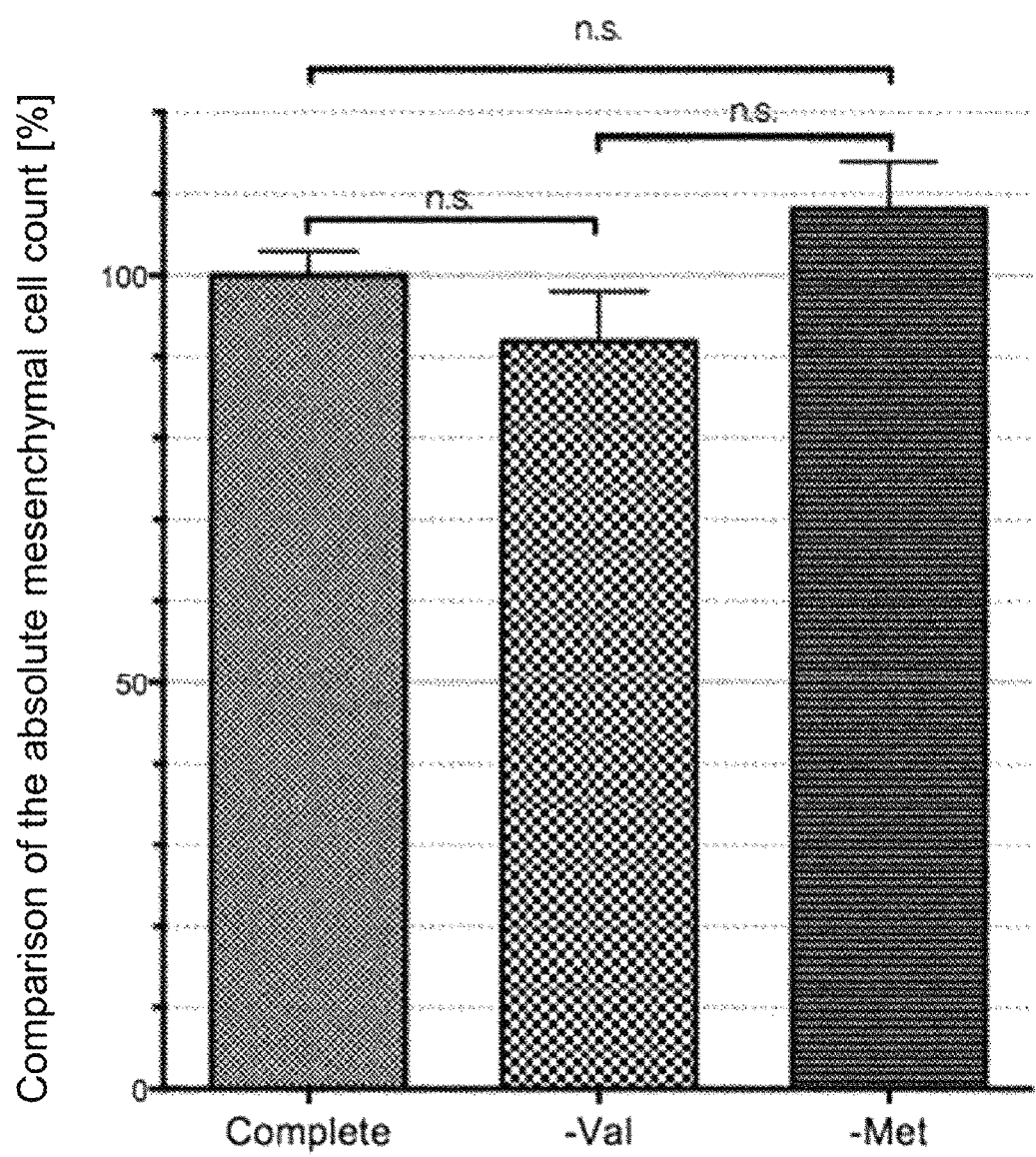
FIG. 5 shows the impact of the culture conditions free of valine or methionine on mesenchymal cells cocultured with the cells of FIG. 4A or B.

By contrast, when measuring the number of cocultured mesenchymal cells, as shown in FIG. 5, no impact of the lack in valine or methionine was observed on mesenchymal cells.

Example 2

Effect of Feed Deficient in Valine or Methionine on the Proliferation of ATL Cells In Vivo In Example 1, the effect of the lack of valine or methionine was examined under culture conditions. In the present example, the impact on the proliferation of ATL cells in vivo was examined by providing feed deficient in valine or methionine to mice transplanted with cells from ATL patients.

Figure 7A:
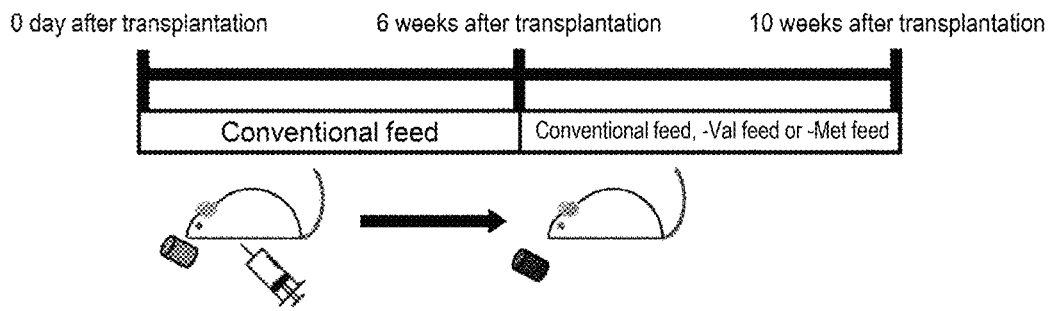
FIG. 7A shows the feeding plan for human ATL cell grafted model.

The compositions of the feed given had the product numbers and compositions as shown in FIG. 6 and were purchased from Research Diet. 100,000 subcultured ATL cells from acute ATL patients were transplanted to adult NOG (NOD/Shi-scid, IL-2RγKO)) mice (12 weeks old, female, n=9) by intraperitoneal administration (i.p.). As shown in FIG. 7A, they were raised on conventional feed for 6 weeks after the transplantation, and from the 6th week after the transplantation, the feed was changed to valine deficient feed, methionine deficient feed or conventional feed, then they were dissected 10 weeks after transplantation and the major diameter of the peritoneal tumor was compared. The results were as shown in FIG. 7B.

Figure 7B:
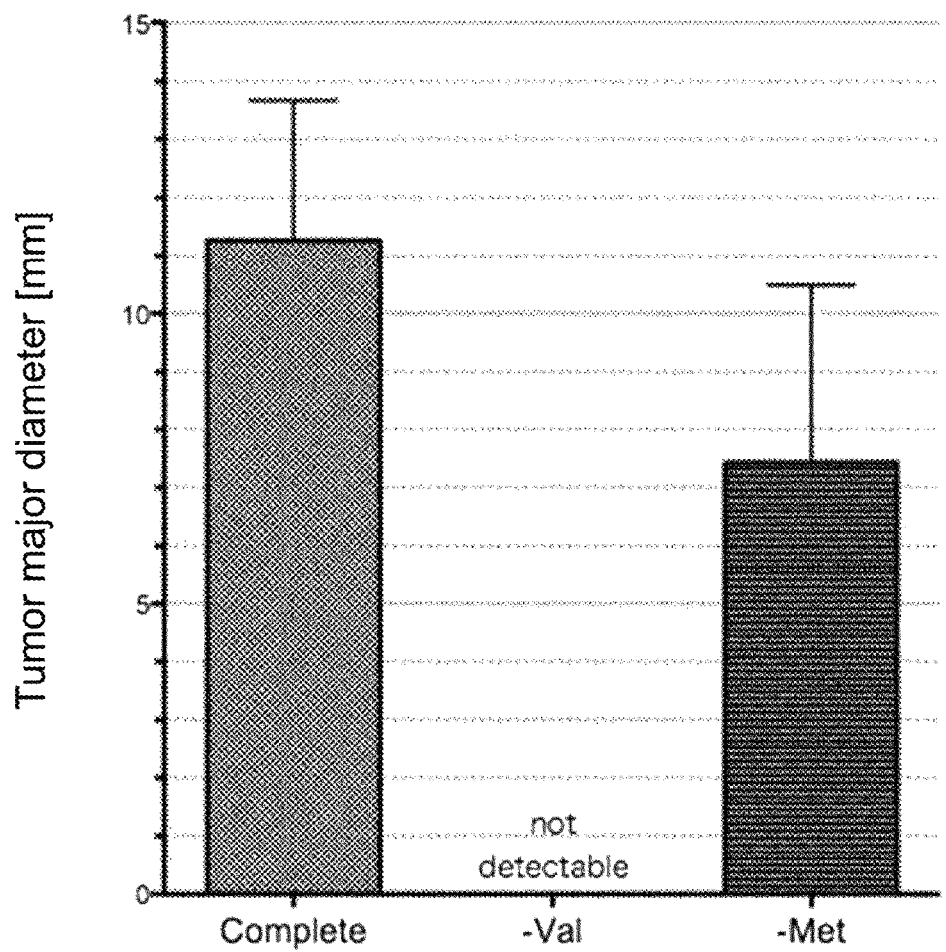
FIG. 7B shows the impact of the culture conditions free of valine or methionine on the size of the tumor caused by ATL cells in human ATL cell grafted model.

As shown in FIG. 7B no clear tumor was observed with the naked eye in mice given valine deficient feed. By contrast, a tumor was observed in mice given methionine deficient feed, but its major diameter was smaller compared to the major diameter of the tumor found in mice given conventional feed.

This made clear that ATL can be treated in vivo by making the feed deficient in either valine or methionine.

Example 3

Figure 8A:
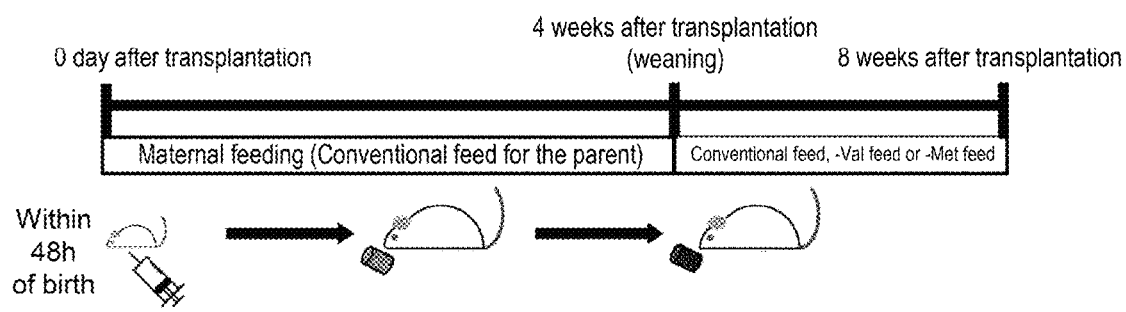
FIG. 8A shows the feeding plan for human ATL cell grafted newborn model.
Figure 8B:
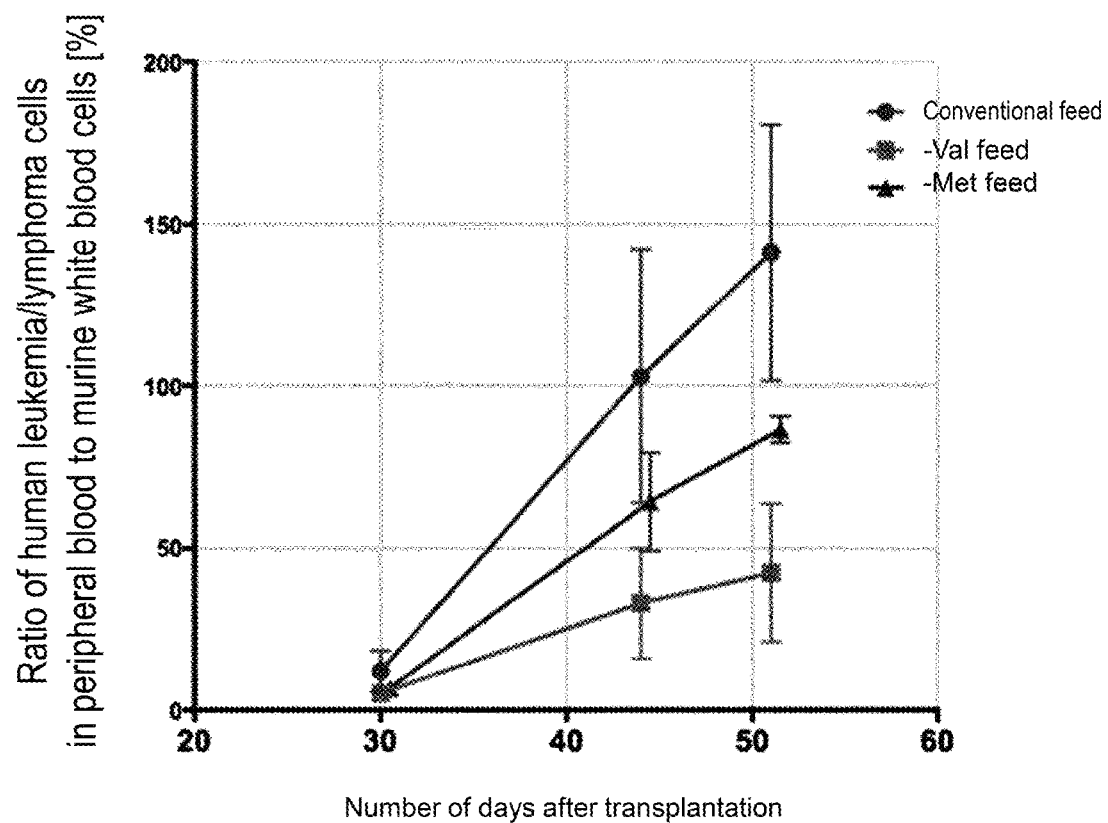
FIG. 8B shows the impact of the culture conditions free of valine or methionine on the proliferation of ATL cells in the peripheral blood of human ATL cell grafted newborn model.

Tumor Suppression in ATL Patient Model 30,000 ATL cells (CD4 positive CADM1 positive fraction), purified and separated using flow cytometry & sorting from peripheral blood of acute ATL patients, were each transplanted intravenously (i.v.) to newborn NOG (NOD/Shi-scid, IL-2RγKO) mice within 48 h of birth. As shown in FIG. 8A, from the 4th week after the transplantation, the feed was changed to valine deficient feed, methionine deficient feed or conventional feed as described in FIG. 6 along with weaning. After transplantation, the change in the ratio of ATL cells in the peripheral blood was regularly evaluated using flow cytometry The results were as shown in FIG. 8B. As shown in FIG. 8B, this made clear that the ratio of ATL cells to mice white blood cells decreases by making the feed deficient in either valine or methionine. Especially, the ratio of ATL cells significantly decreased when giving valine deficient feed.

Figure 8C:
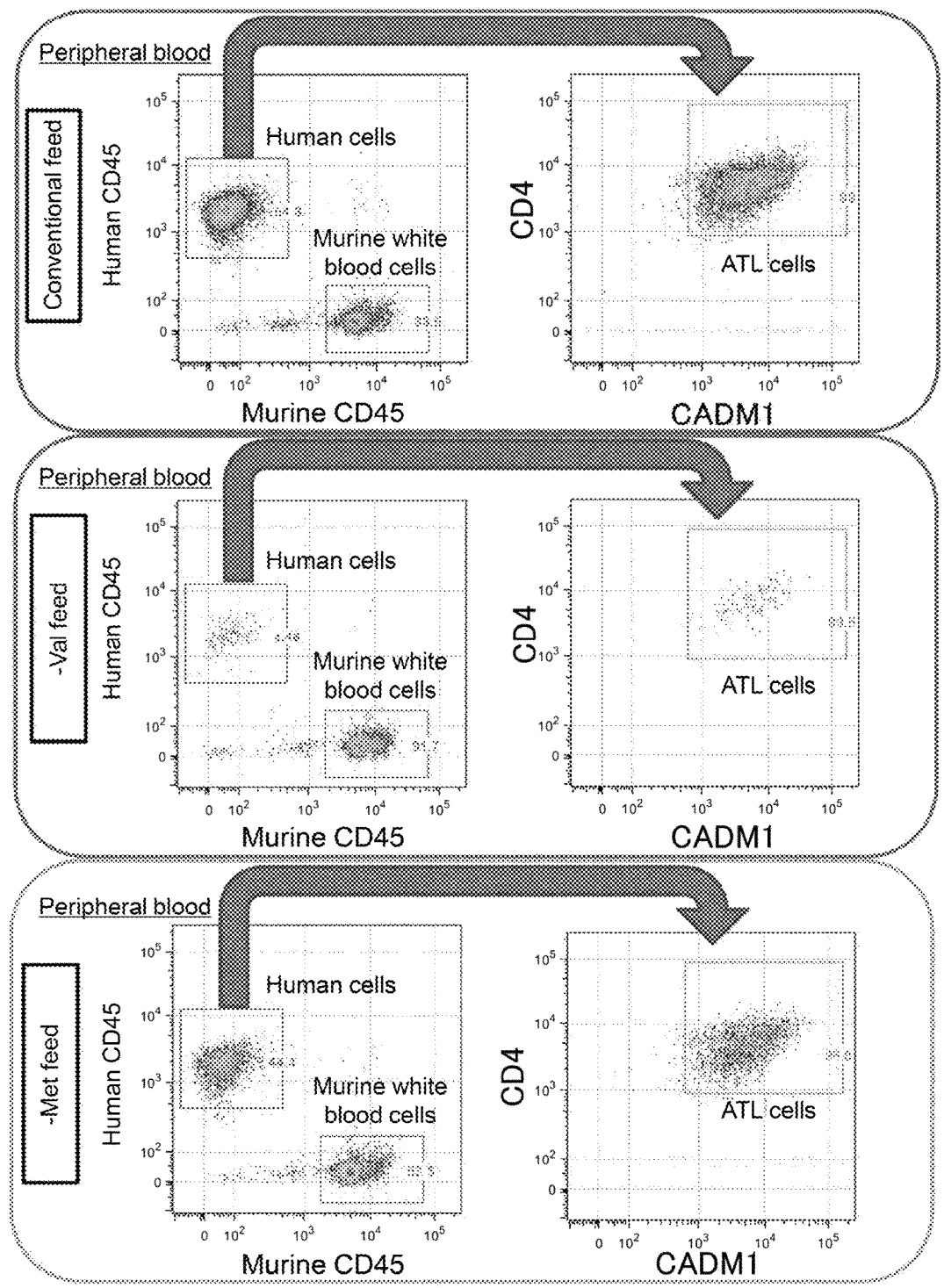
FIG. 8C shows that the number of human CD45-positive cells (ATL cells) in the peripheral blood of human ATL cell grafted newborn model can be decreased by culture conditions free of valine or methionine.

Moreover, the peripheral blood was analyzed by flow cytometry 8 weeks after transplantation. The results were as shown in FIG. 8C. As the results of the mice given conventional feed of FIG. 8C suggest, the human cells (human CD45 positive cells) observed in the peripheral blood of the above ATL model mice were all CD4+ CADM1+ and were ATL cells.

By contrast, the number of CD4 positive CADM1 positive cells clearly decreased in mice given valine deficient feed, compared to the number of cells when giving conventional feed (see FIG. 8C, −Val feed). Moreover, the number of CD4 positive CADM1 positive cells decreased in mice given methionine deficient feed, compared to the number of cells when giving conventional feed (see FIG. 8C, −Met feed).

Further analysis was conducted. The number of ATL cells, hemoglobin (Fib) concentration and platelet count (Plt) was examined at the 8th week after transplantation in each above mouse. The results were as shown in FIG. 8D.

Figure 8D:
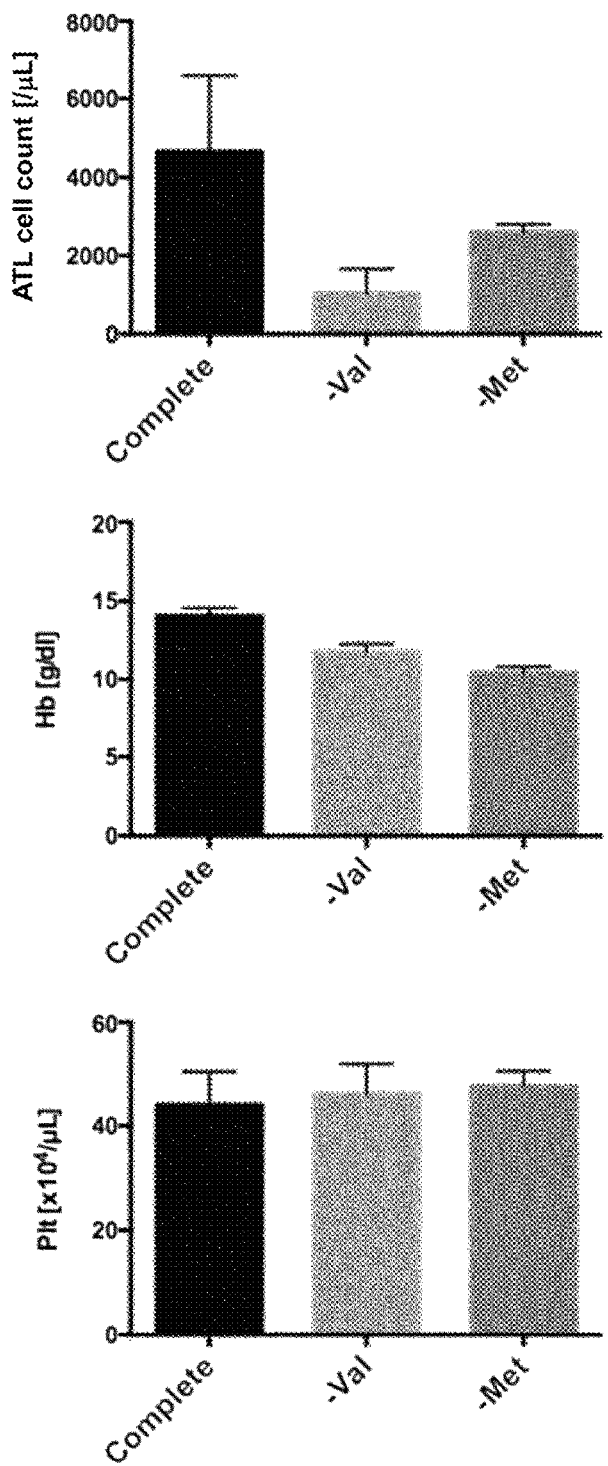
FIG. 8D shows the impact of the culture conditions free of valine or methionine on the number of ATL cells, the hemoglobin (Hb) concentration and the platelet (Plt) count in the peripheral blood of human ATL cell grafted newborn model.

As shown on the upper panel of FIG. 8D, ATL cells decreased by giving feed deficient in either valine or methionine.

As shown on the middle panel and lower panel of FIG. 8D, there was no significant change in the hemoglobin concentration and the platelet count by making the feed deficient in valine and methionine.

Moreover, the degree of invasion of ATL cells in the skin, the liver and the spleen of the mice 8 weeks after the transplantation was compared between mice given conventional feed and mice given valine deficient feed by tissue section. Concretely, for the tissue sections prepared from each mice, the tissues were observed by haematoxylin eosin (HE) staining and immunohistochemical staining using anti-human CD4 antibody (CD4 positive ATL cells are shown in brown). The results were as shown in FIG. 9.

Figure 9:
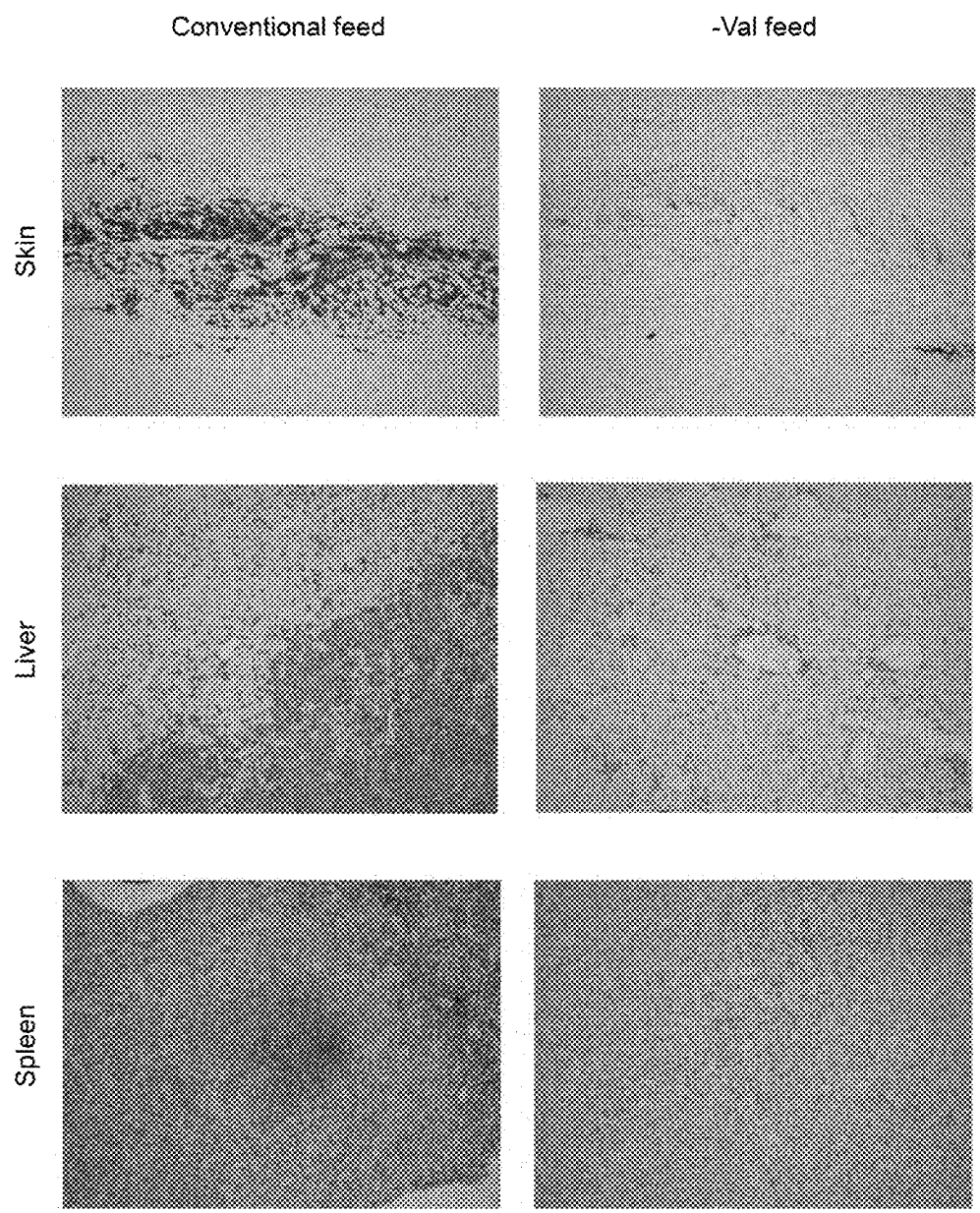
FIG. 9 shows an immunohistochemical staining to evaluate the invasion of ATL cells in each tissue of human ATL cell grafted newborn model.

As shown in FIG. 9, in mice given conventional feed, the ATL cells were observed to have significantly invaded all tissues such as skin, liver and spleen (the greater part of the tissues is stained in brown). However, in mice given valine deficient feed, the amount of ATL cell invasion was significantly decreased in all the tissues (the brown stained image is only visible sparingly).

This showed that, when providing neither valine nor methionine, the cell number of ATL cells not only decreases, but the invasion to the tissues also decreases and the organ invasion of ATL cells can be inhibited.

As shown above, it was found that valine and methionine are necessary to the proliferation of HTLV-1 infected T cells and ATL cells respectively. Moreover, it was found that the proliferation of these cells is actually inhibited by removing valine and methionine from the source of nutrition.

Example 4

Decrease in the Number of Hematopoietic Stem Cells by Providing No Valine

When medically treating ATL patients by hematopoietic stem cell transplant therapy, in addition to the reduction of ATL cells, it is necessary that the engraftment of hematopoietic stem cells contained in the graft (donor) to the bone marrow of the patient (recipient) be successful. For that, it is necessary to decrease the hematopoietic stem cells of the recipient to make space for the engraftment of the hematopoietic stem cells of the donor, as well as to pretreat to decrease the lymphocytic cells to prevent a rejection of the graft by the immunity. In the present example, the reduction of hematopoietic stem cells and lymphocytic precursor cells in mice given feed free of valine was evaluated to evaluate the situation of the hematopoietic stem cells in the patient's body when applying the method of the present invention to an ATL patient receiving hematopoietic stem cell transplant therapy.

The feeds had the product numbers and compositions as shown in FIG. 6 and were purchased from Research Diet. First, the content of each amino acid in the peripheral blood and bone marrow of mice fed for four weeks with conventional feed or feed free of valine, was measured.

The peripheral blood samples for the measurement of amino acid content were obtained by centrifuging the blood sampled from an eye orbit and removing the cell components, then removing the protein components using an Amicon Ultra-0.5 mL Centrifugal Filter (Merck Millipore). The bone marrow samples for the measurement of amino acid content were obtained by eluting the bone marrow with water, then removing the proteins using an Amicon Ultra-0.5 mL Centrifugal Filter. The content of each amino acid in these samples were measured using Prominence Amino Acid Analysis System (Shimadzu).

Figure 10:
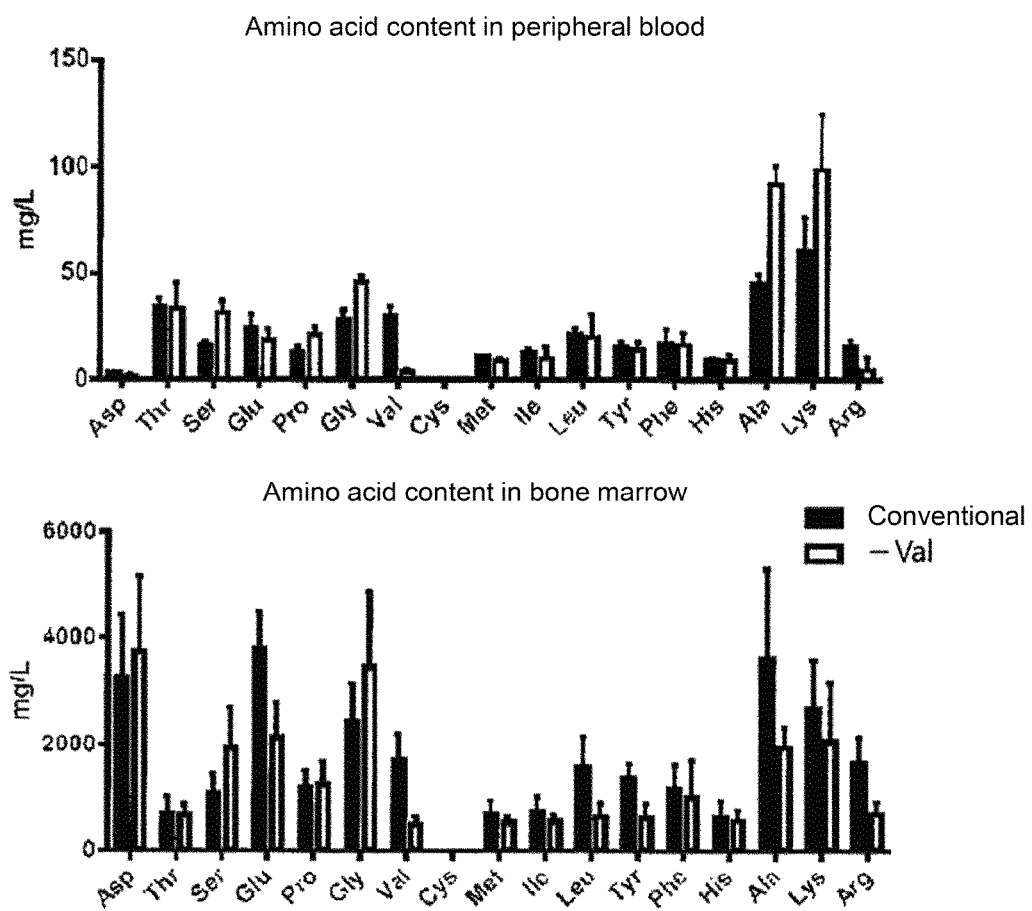
FIG. 10 shows the results of investigating the amino acid content in the peripheral blood or bone marrow of mice fed for four weeks with conventional feed and feed free of valine (−Val), respectively.

The results were as shown in FIG. 10. As shown in FIG. 10, the valine content decreased in both peripheral blood and bone marrow of mice given feed free of valine for four weeks.

Furthermore, the number of hematopoietic stem cells in mice given feed free of valine for four weeks was also investigated. As the hematopoietic stem cells, CD150+ CD41-CD48-KSL cells were obtained by the following method. First, bone marrow cells were collected from B6 mice given feed free of valine for four weeks. The cells were stained with the above lineage marker cocktail, APC conjugated anti-c-kit antibody, pacific blue conjugated anti-Sca-1 antibody, FITC-conjugated anti-CD41 antibody, Alexa Fluor 488-conjugated anti-CD48 antibody and PE-conjugated anti-CD150 antibody, as well as Streptavidin-APC-eFluor 780 antibody.

The measurement of the cell number was conducted with FACS Aria II SORP (BD Biosciences), and analyzed using FlowJo Software (Tree Star).

Figure 11:
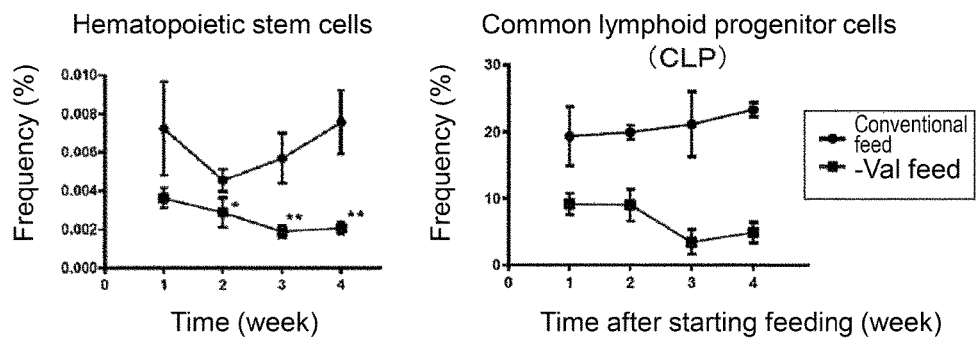
FIG. 11 shows the presence frequency of hematopoietic stem cells and common lymphoid progenitor cells in the bone marrow obtained from mice fed for four weeks with conventional feed or feed free of valine.

As a result, as shown in FIG. 11, the frequency of hematopoietic stem cells significantly decreased in mice given feed free of valine. Moreover, a significant decrease was observed in the frequency of common lymphoid progenitor (CLP) cells in mice given feed free of valine.

Figure 12A:
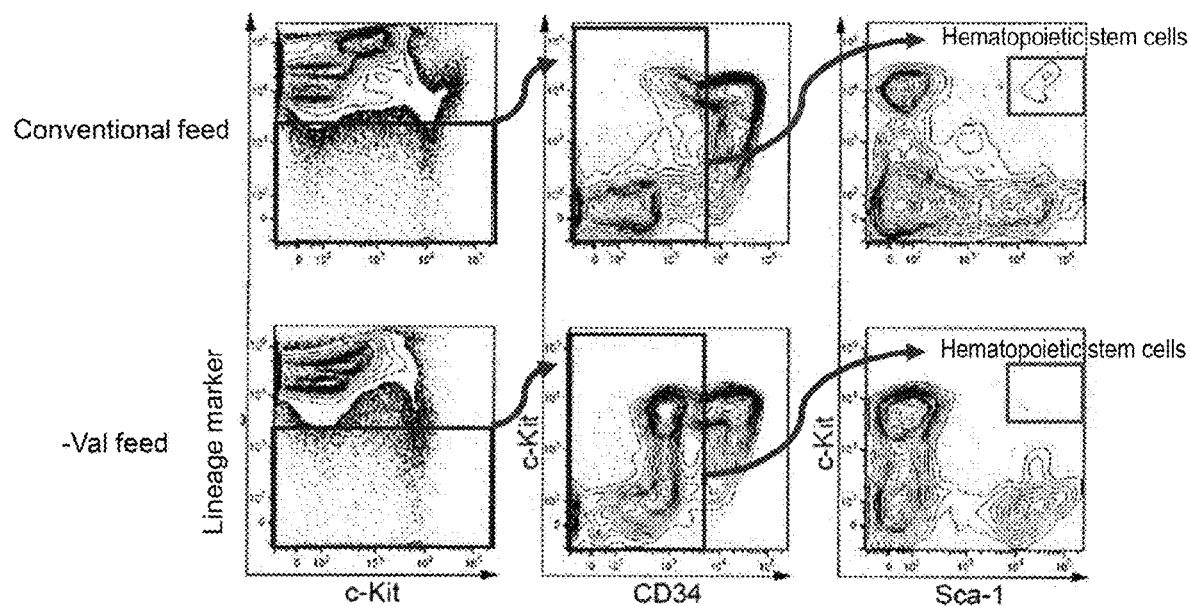
FIG. 12A shows the expansion plan of hematopoietic stem cells in the bone marrow of mice fed for four weeks with conventional feed or feed free of valine (−Val).
Figure 12B:
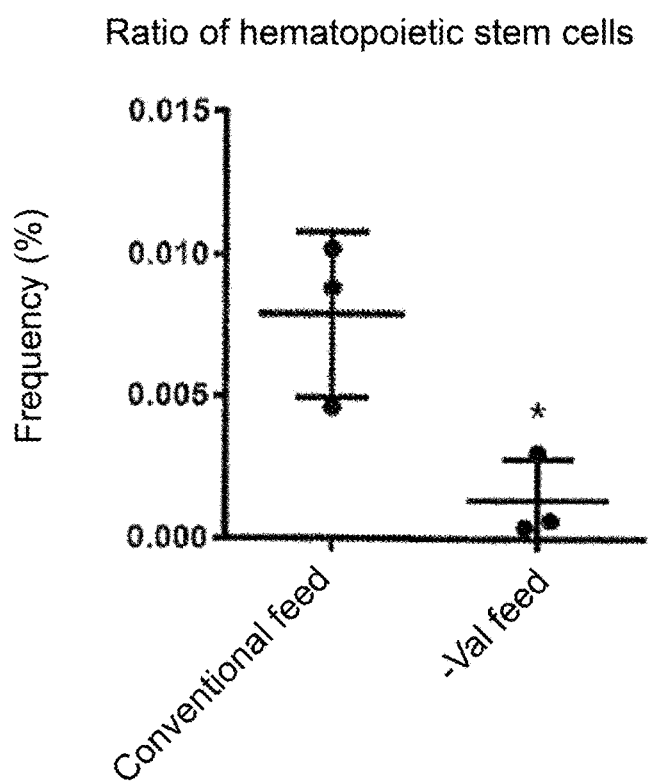
FIG. 12B shows the presence frequency of hematopoietic stem cells.

Furthermore, when examining the frequency of CD34-KSL hematopoietic stem cells, in mice given feed free of valine, the fraction of CD34-KSL hematopoietic stem cells was small as shown in the expansion example of FIG. 12A and the ratio of hematopoietic stem cells had also decreased as shown in FIG. 12B. This made clear that it is possible to decrease the hematopoietic stem cells at a sufficient level as a pretreatment for hematopoietic stem cells transplant, by providing no valine.

As described above, it was found that the reduction of hematopoietic stem cells, necessary before performing a hematopoietic stem cell transplant in ATL patients, is possible by removing valine from the source of nutrition.

Namely, by nutritionally managing ATL patients for a prescribed time period by providing no valine, in addition to be able to decrease the ATL cells in the body, it is also possible to decrease the hematopoietic stem cells in the body at a sufficient level as a pretreatment for hematopoietic stem cells transplant. Therefore, by managing his nutrition for a prescribed time period by providing no valine, an ATL patient can avoid excess administration of anti-cancer drugs (in some cases, can completely avoid the administration of anticancer drugs), and can reduce the intensity of the chemotherapy or radiation therapy that has been conventionally given to decrease hematopoietic stem cells, or completely avoid chemotherapy or radiation therapy, and significantly reduce the side effects of the treatment.

The invention claimed is:

1. A method for treating a subject infected with HTLV-1 virus, comprising:
    administering a complete nutrition formulation by enteral and/or parenteral administration, to the subject,
    wherein the complete nutrition formulation includes
        a sugar,
        a vitamin,
        electrolytes,
        amino acids including tryptophan, lysine, phenylalanine, threonine, leucine, isoleucine and histidine, and
        at least one essential trace element selected from the group consisting of iron, zinc, copper, selenium, chromium, cobalt, iodine, manganese and molybdenum, and the complete nutrition formulation is substantially free of at least one of valine and methionine, and
    the subject's diet is restricted to the complete nutrition formulation only for a time sufficient to decrease a number of HTLV-1 virus infected cells.

2. The method of claim 1, wherein the complete nutrition formulation is substantially free of both valine and methionine.

3. The method of claim 1, wherein the subject has adult T cell leukemia/lymphoma.

4. The method of claim 1, wherein the subject is an HTLV-1 carrier before developing adult T cell leukemia/lymphoma.

5. The method of claim 2, wherein the subject has adult T cell leukemia/lymphoma.

6. The method of claim 2, wherein the subject is an HTLV-1 carrier before developing adult T cell leukemia/lymphoma.

7. The method of claim 1, wherein the amino acids further include asparagine, aspartic acid, serine, glutamine, glutamic acid, proline, glycine, tyrosine, alanine, cysteine and arginine.

8. The method of claim 2, wherein the amino acids further include asparagine, aspartic acid, serine, glutamine, glutamic acid, proline, glycine, tyrosine, alanine, cysteine and arginine.

* * * * *